United States Patent [19]

Wrobel et al.

[11] Patent Number: 5,475,197
[45] Date of Patent: Dec. 12, 1995

[54] PROCESS AND APPARATUS FOR THE ABLATION OF A SURFACE

[75] Inventors: Walter Wrobel, Aalen; Theo Lasser, Oberkochen; Peter Reimer, Ellwangen; Herbert Gross; Willi Ulrich, both of Aalen, all of Germany

[73] Assignee: Carl-Zeiss-Stiftung, Heidenheim, Germany

[21] Appl. No.: 77,282

[22] Filed: Jun. 14, 1993

[30] Foreign Application Priority Data

Jun. 17, 1992 [DE] Germany .................. 42 19 809.7

[51] Int. Cl.[6] .................................................. B23K 26/06
[52] U.S. Cl. .................. 219/121.69; 219/121.61; 219/121.66; 219/121.75
[58] Field of Search ............ 219/121.68, 121.69, 219/121.85, 121.65, 121.66, 121.73, 121.75, 121.61; 372/9

[56] References Cited

U.S. PATENT DOCUMENTS

| | | | |
|---|---|---|---|
| 4,154,530 | 5/1979 | Connolly, Jr. et al. | 356/152 |
| 4,566,765 | 1/1986 | Miyauchi et al. | 350/619 |
| 4,670,639 | 6/1987 | Behn | 219/121.68 |
| 4,732,148 | 3/1988 | Esperance, Jr. | 128/303.1 |
| 5,256,853 | 10/1993 | McIntyre | 219/121.75 |

*Primary Examiner*—Mark H. Paschall

[57] ABSTRACT

For defined ablation of a surface, successive partial regions of equal surface area are acted on by a radiation source, preferably a laser, through an optical system. The partial regions are smaller as regards surface area than the whole surface to be processed, so that the respective radiation source can be dimensioned in a less costly manner. Telescope optics with conical surfaces serve as optical systems suitable for this purpose.

12 Claims, 3 Drawing Sheets

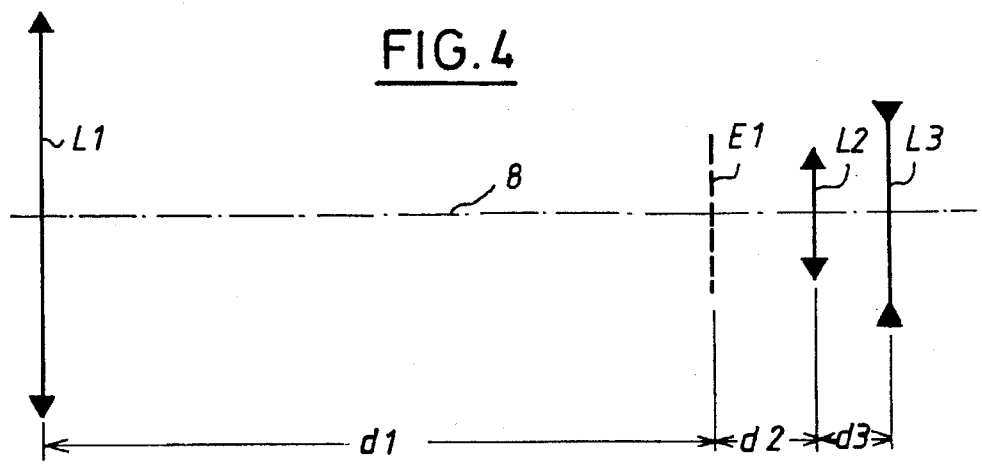
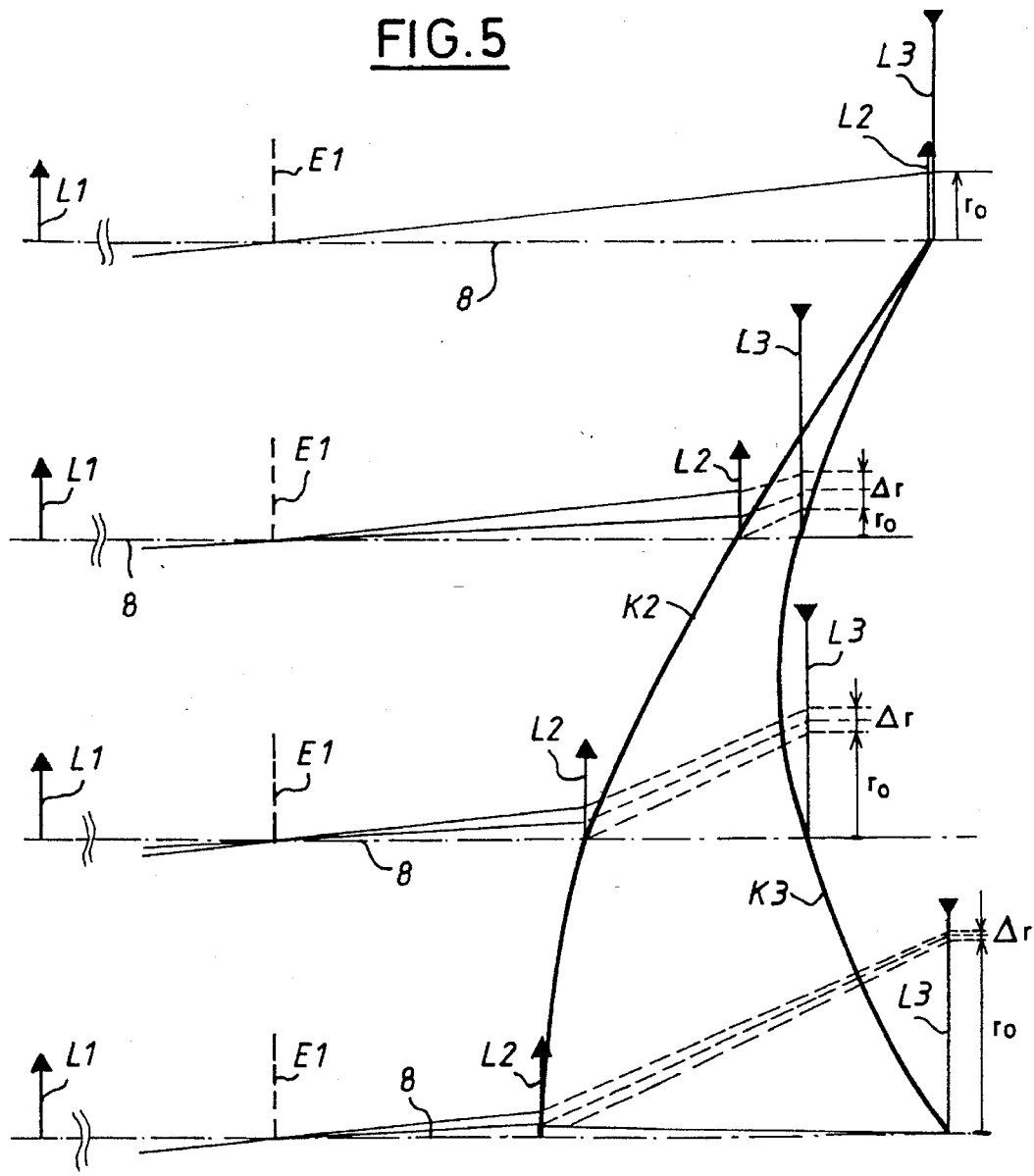

PROCESS AND APPARATUS FOR THE ABLATION OF A SURFACE

FIELD OF THE INVENTION

This invention relates to a process for the ablation of a surface by means of electromagnetic radiation and to suitable apparatus for carrying out the process.

BACKGROUND OF THE INVENTION

Processes and apparatus are known from U.S. Pat. No. 4,941,093 with which a defined ablation of surfaces is possible. In particular, processes and apparatus are described in this patent that make possible a defined ablation of the cornea. The optical properties of the cornea are to be modified in this manner such that errors of vision such as hyperopia or myopia can be corrected. This is effected in that the beam cross section of a laser beam which impinges on the cornea is modified in shape and size in the course of time such that a cumulative ablation effect on the affected surface results in the desired new surface profile. The processes described in this patent provide a variation during the course of time, in succession from initially larger affected surfaces of varied shapes towards smaller affected surfaces, or vice versa. In such processes, the radiation source used, i.e., a laser, must be designed such that a sufficient energy density over the whole beam cross section is available for even the largest affected surface. For the laser system used, and in particular for the proposed excimer laser, there is an immense apparatus cost as soon as it is desired to process large surfaces with it.

Furthermore, it is known from DD-Patentschrift (East German patent) 263,447 to make use of an axicon pair in combination with a cylindrical lens array in order to reduce the technical equipment cost in the operative treatment of the cornea. This arrangement is however primarily suitable for the positioning of cut patterns in the cornea, i.e., less suitable for the ablation of surfaces.

SUMMARY OF THE INVENTION

It is therefore the object of the present invention to provide a process and suitable apparatus that make possible a defined ablation of a surface with electromagnetic radiation and in this connection keep as low as possible the cost of the apparatus relating to the radiation source and also the optical elements.

In the process according to the invention, the surface to be processed is divided into individual partial regions of respectively equal area, which are acted on in succession by the radiation source with the same power, in irradiation steps following one after the other. The optical system used for this purpose must ensure that partial regions, always of equal surface area, are acted on on the surface to be processed in order to obtain a defined ablation profile. The desired ablation profile is achieved in that respectively, different ablation characteristics result by means of different irradiation time periods for the individual partial regions. A desired overall ablation profile can be realized in this manner. The advantage of the process according to the invention is that the maximum available power of the radiation source does not have to be applied to the whole surface to be processed, but only to a significantly smaller partial region of this surface. The use of a substantially more compact radiation source is thus possible. Moreover, the radiative power can be kept constant during successive action on partial regions of the same size, so that at the same time an equal average intensity on the respective partial region is always ensured.

In particularly suitable processes for the processing of a rotationally symmetrical surface region, a circular overall surface, within which a defined ablation profile is to be attained, is divided in successive partial irradiation steps into circular or annular partial regions of equal surface area, which are acted on for a respective given time. This process is particularly advantageous for the specific ablation of the cornea during refractive surgery, and in the processing and production of Fresnel lenses.

Suitable apparatus or optical systems for carrying out the process according to the invention both make possible a widening or an enlargement of the entering beam cross section and ensure the defined transformation of the circular entering beam cross section. Furthermore, the respective optical systems of the apparatus according to the invention are designed such that the surface of the exit beam cross section is always approximately constant.

BRIEF DESCRIPTION OF THE DRAWINGS

Further advantages, and also details of the process according to the invention and of suitable apparatus for carrying out this process, will be fully understood from the following description of preferred embodiments with reference to the accompanying drawings, in which:

FIG. 4 shows a schematic representation of a suitable optical system for the definition of the relevant system parameters; and FIG. 5 shows the varying of the exit beam parameters during passage along given control curves with individual elements of the optical system of FIG. 4.

DETAILED DESCRIPTION

Figure 1:
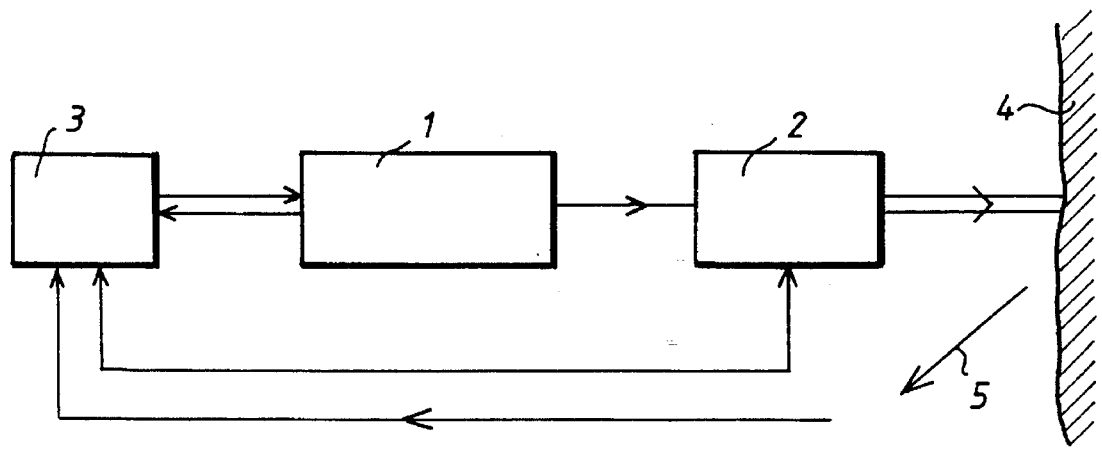
FIG. 1 shows a shematic representation of an apparatus that is suitable for carrying out the process according to the invention.
Figure 2:
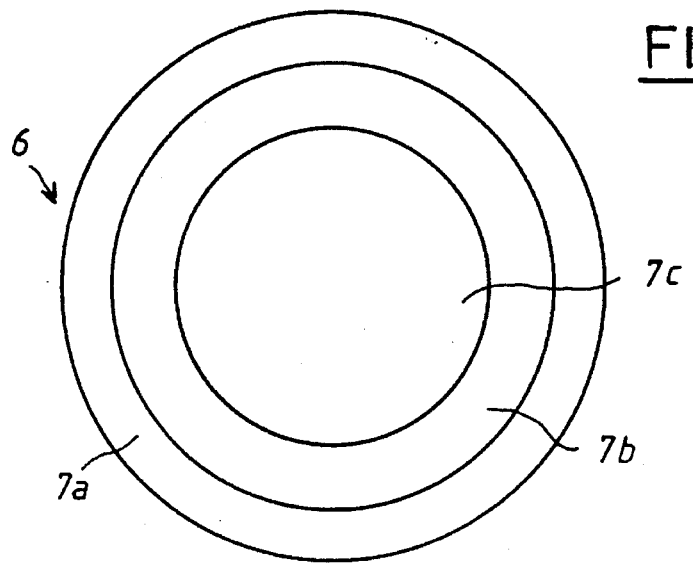
FIG. 2 shows rotationally symmetrical partial regions, which are successively acted on, of a surface to be processed.

An apparatus with the required individual components, suitable for carrying out the process according to the invention is shown in FIG. 1. A laser that emits pulses of coherent electromagnetic radiation is the radiation source (1). For example, an excimer laser which operates in the UV region of the electromagnetic spectrum is suitable for ablation of the cornea. A defined so-called photoablation of the surface to be processed (4) can be effected by means of a laser that emits in this wavelength region. Furthermore, it is possible to use a laser operating in the infrared region of the electromagnetic spectrum between 800 nm and 3000 nm, for example a Ho:YAG-laser, a Ho:YLF-laser, an Er:YAG-laser, an Er:YLF-laser, a Th:YAG-laser or a Nd:YAG-laser. An optical system (2) is provided between the radiation source (1) and the surface to be processed (4). Optical systems that are suitable for this purpose are described in further detail below. A control device (3) e.g., a suitable computer, controls the radiation source, in particular, control of the pulse sequence and pulse power. Moreover, the specific control of the optical system (2) takes place by means of the control device (3) to carry out the process according to the invention. It is also possible to monitor the ablation process quantitatively on the surface to be processed (4) through the control device (3), which is schematically indicated in FIG. 1 by the arrow (5). In monitoring of this kind, the present actual ablation is compared with the desired reference ablation and is repeatedly corrected by control device (3) in a control circuit. As an example, how a circular region on an optional surface can be subjected to a defined ablation with the aid of the process according to the invention is explained below with reference to FIG. 2, Such a process can for example be used in refractive corneal surgery or in the processing of Fresnel lenses. Thus, for example, a flattening of a spherical surface, which is required for correction of myopia by corneal surgery, is achieved with the aid of the process according to the invention.

A given volume of material is to be ablated for this purpose within the circular region (6) on an optional surface, such that a defined surface profile within this region (6) then results. As has already been indicated, this can mean a flattening in comparison with the surface profile heretofore.

According to the invention, the ablation process proceeds in several successive individual steps, which are determined by the control device based on the desired or predetermined final ablation profile. Partial regions of a circular or annular shape, with equal surface area, are acted on by the emitted laser pulses in the individual partial irradiation steps. By keeping constant the surface area acted on in the individual partial irradiation steps, it is possible to attain with equal power of the radiation source a constant average intensity and consequently a defined ablation result. The surface to be processed can, for example, be acted on during three successive partial irradiation steps, first in a circular region (7c) for a given time period $\Delta t_1$. The irradiation of an annular partial region (7b) of equal surface area, which adjoins the first irradiated circular area (7c), then takes place for a given time period $\Delta t_2$. In a third processing step, the irradiation of a third, likewise annular, partial region (7a) of likewise equal surface area is finally carried out for a given time period $\Delta t_3$. The individual partial regions (7a, 7b, 7c) are respectively acted on by pulses of coherent electromagnetic energy until the desired ablation profile in each partial region has been attained. The individual durations of the action $\Delta t_i$ can vary throughout, according to the desired ablation profile. Besides action on the individual partial regions from the inside outwards, as just described, it is also possible, for example, to first irradiate the outermost annulus (7c). Then follows the adjoining middle annulus (7b), while the circular central region (7c) is acted on in conclusion.

By varying the periods $\Delta t_i$ of action and/or the sequence of the irradiated partial regions, both the described flattening and a steeper surface profile can be realized in the processed surface region.

Since each of the partial regions (7a, 7b, 7c) acted on have a smaller surface than the whole region to be processed (6), it is possible to dimension the radiation source used in a less costly manner, as regards power. According to the desired ablation profile or the available power of the radiation source, a division of the surface region to be processed into still more partial regions can be necessary or useful. The ablation result is then determined at any given time by the cumulative total volume of ablated material.

The realization of the individual partial regions of constant surface area takes place with the aid of optical systems (as explained hereafter) that are controlled by the control device in a defined manner during the course of time, in order to maintain a desired beam cross section on the surface to be processed.

Suitable optical systems for carrying out the process according to the invention will be described with reference to FIG. 3a and FIG. 3b. Both the optical system shown in FIG. 3a and that shown in FIG. 3b ensure that a beam bundle entering parallel to the optical axis (8) with a circular cross section, e.g., a collimated laser beam, is transformed into an emergent beam bundle, likewise parallel to the optical axis (8), with a defined, annular beam cross section. No imaging occurs on the surface to be processed. At the same time, the entering beam cross section is enlarged, with the transformed, annular beam cross section however always having approximately the same surface area. The selected sizes of the surface areas acted on, i.e., of the effective beam cross section, is determined by the respective enlarging action of the optical system used. These requirements for a suitable optical system are fulfilled by the two embodiments shown in FIG. 3a and FIG. 3b. For this purpose a two-part telescope optics with conical surfaces, i.e., a transmissive axicon arrangement, is provided. In principle, the use of a reflective axicon arrangement is likewise possible. The corresponding dimensioning of the individual optical components (9, 10a, 10b; 11a, 11b) of the optical system permits the above requirements to be fulfilled with only two optical elements (10a, 10b; 11a, 11b), which are displaceable along the optical axis (8). The control curves of the two displaceable optical elements (10a, 10b; 11a, 11b) are correlated with one another by a control device (3) such that the constancy of surface area is ensured with adjustable annulus parameters that are defined at the same time.

Figure 3A:
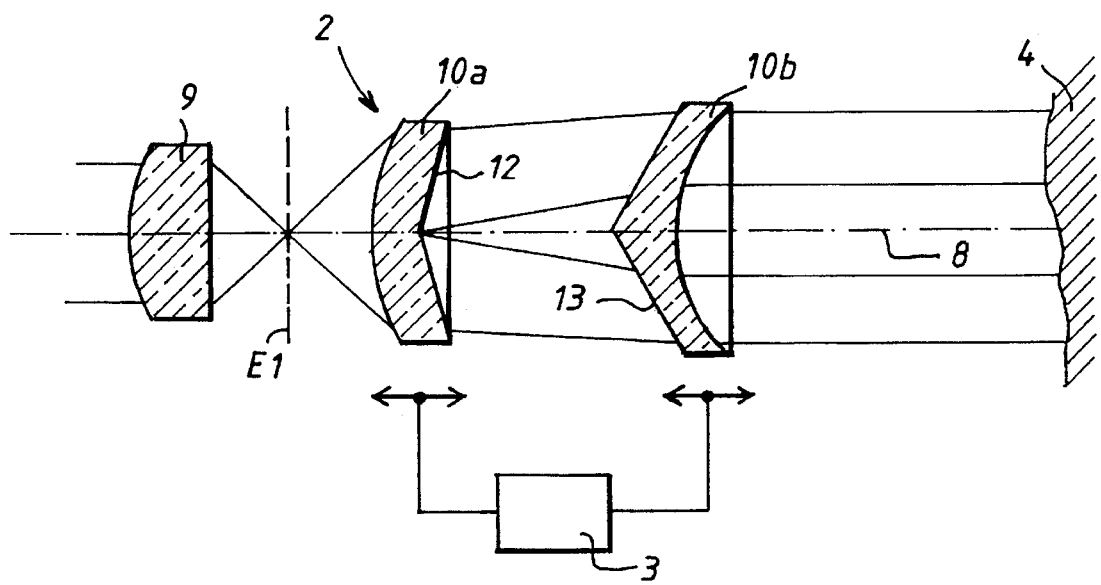
FIG. 3a and 3b respectively show a preferred embodiment of an optical system for carrying out the process according to the invention.

The first optical system according to the invention, in FIG. 3a, includes a first, stationary optical element (9) with focusing action, e.g., a planoconvex lens. This first optical element (9) supplies, in the plane E1, a real intermediate image of the entering beam bundle. Following this there are arranged in the direction of beam propagation a second optical element (10a) with positive refractive power and a diverging conical surface (12), and a third optical element (10b) with negative refractive power and a converging conical surface (13). The conical surfaces of the second and third optical elements face each other. A planoconvex lens with a diverging cone action is an alternative as the second optical element (10a); a planoconvex lens with a converging cone action can be used as the third optical element (10b). The second and third optical elements (10a, 10b) are respectively displaceable along the optical axis (8) in a defined manner by the control device (3). The predetermined, defined control curves for these relative motions ensure the fulfillment of the requirements stated above. After passing through the optical system (2), the beam transformed in this manner impinges on the respective surface to be processed (4).

The focusing first optical element (9) accordingly forms, with the second and third optical elements (10a, 10b) a telescope system with variable magnification, and the control curves of the displaceable optical elements (10a, 10b) ensure that the constancy of surface area of the partial regions acted on is within given limits.

Figure 3B:
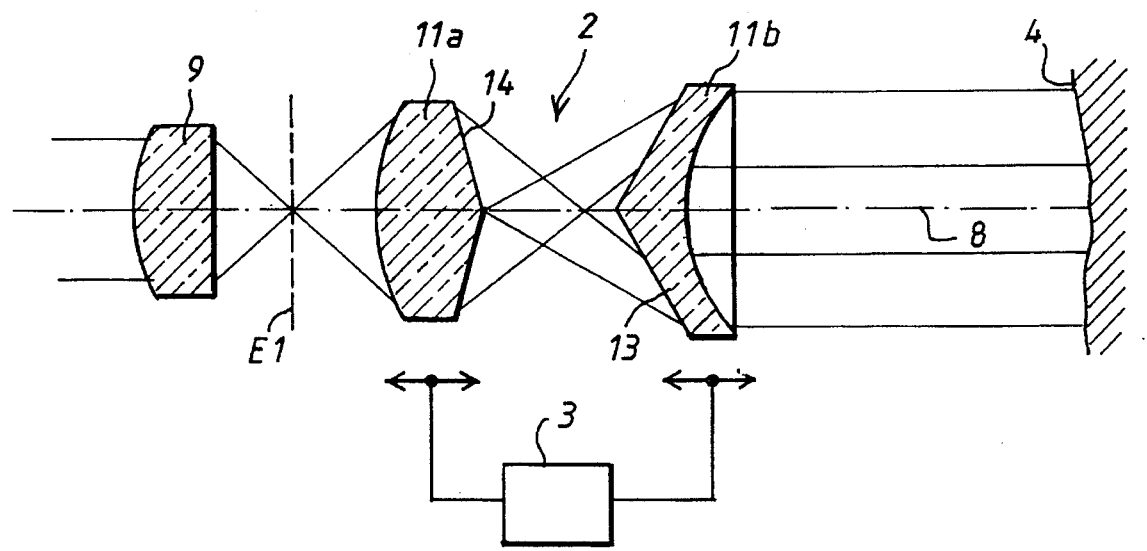

A second embodiment of a suitable optical system is shown in FIG. 3b, in which the same symbols have been selected for the same elements as in FIG. 3a. The first, focusing optical element (9) is followed by a first optical element (11a) with positive refractive power and a converging conical surface (14). There is likewise again provided, as the third optical element (11b) in the beam path, an optical element (11b) with negative refractive power and a converging conical surface. The two conical surfaces (14, 15) in this embodiment are again mutually facing; however, this is not in general absolutely necessary. The control device (3) effects the defined displacement of the second and third optical elements (11a, 11b) along the optical axis (8). The transformed beam, after passing through the optical system, again reaches the surface to be processed (4). The manner of functioning is in principle identical with that of the optical system of FIG. 3a, with the exception of the different optical action of the second optical element (11a).

Another embodiment of the optical system according to the invention will be described below, with reference to FIGS. 4 and 5, for a given, predetermined focal distance $f_1=100$ mm of the first, converging optical element (9). In particular, the control curves of the two displaceable elements (10a, 10b; 11a, 11b), which are varied by the control device (3) in a defined manner, are illustrated.

The optical magnitudes that are used below are defined for this purpose in FIG. 4. The optical system according to the invention consists of the first, stationary, focusing optical element L1 and the optical elements L2 and L3, which are variable within given limits, along the optical axis (8), and which have focusing or diverging optical actions. The (fixed) focal distance (100 mm) of the first focusing optical element L1, to which the remaining data are normalized below, is denoted by $d_1$ or $f_1$. The distance of the element L2 from the focal plane E1 is denoted by $d_2$, while $d_3$ characterizes the distance between L2 and L3. For a telescope factor $\beta=0.2$, the two variable optical elements L2 and L3 are displaceable along given control curves K2 and K3 between a defined initial position with $$d_2=\beta \cdot d_1$$

and $$d_3=0$$

and the final position with $$d_2=0.082 d_1$$

and $$d_3=0.122 d_1,$$

With a predetermined focal distance $f_1=100$ mm of the first optical element L1, $$d_2=8.2 \text{ mm}$$

and $$d_3=12.2 \text{ mm,}$$

respectively.

With a predetermined focal distance $f_1=100$ mm of the first optical element L1, the variable optical elements L2 and L3 have the focal distances $$f_2=5.88 \text{ mm}$$

and $$f_3=-8.33 \text{ mm,}$$

respectively.

The "passage through" the whole region of adjustment is shown in FIG. 5. The control curves K2 and K3 of the two variable optical elements L2 and L3 are likewise shown or plotted. The inner annulus radius and the annulus width of the emergent beam cross section are respectively denoted in FIG. 5 by $r_0$ or $\Delta r$. While passing along the control curves K2 and K3 from the abovementioned initial position into a defined final position, there result in the emergent beam cross section an increasing inner annulus radius $r_0$ and also a decreasing annulus width $\Delta r$.

We claim:

1. In a process for the ablation of a surface by means of electromagnetic radiation, wherein the surface to be processed is aligned centrally with respect to an optical axis, a radiation source emits pulses of electromagnetic energy along said optical axis and the region of the surface acted on by said electromagnetic radiation is adjustable in a defined manner by means of an optical system, the improvement comprising the steps of:

acting on partial regions of constant area on said surface to be processed in successive sequence by said electromagnetic radiation, arranging said optical system in the beam path of said electromagnetic radiation to ensure the constancy of the surface area of each partial region acted on in each partial exposure, employing a radiation source having a maximum power that is adequate to deliver an electromagnetic energy density in said partial regions of constant area that is adequate to ablate said surface area of each partial region, monitoring actual ablation of said surface area of each partial region quantitatively, comparing said actual ablation with a desired reference ablation, and repeatedly adjusting said actual ablation to correspond to said reference ablation.

2. Process according to claim 1, wherein successive partial regions of rotationally symmetrical shape are acted on, a rotational symmetry being present with respect to the optical axis.

3. Process according to claim 2, wherein the radii of said successive partial regions acted on decrease.

4. Process according to claim 2, wherein the radii of said successive partial regions acted on increase.

5. Process according to claim 1, wherein said electromagnetic radiation lies in the UV region of the electromagnetic spectrum.

6. Process according to claim 1, wherein said electromagnetic radiation lies in the infrared region of the electromagnetic spectrum.

7. In a process for the ablation of a surface by means of electromagnetic radiation, wherein the surface to be processed is aligned centrally with respect to an optical axis, a radiation source emits pulses of electromagnetic energy along said optical axis and the region of the surface acted on by said electromagnetic radiation is adjustable in a defined manner by means of an optical system, the improvement comprising the steps of:

acting on partial regions of constant area on said surface to be processed in successive sequence by said electromagnetic radiation, and arranging said optical system in the beam path of said electromagnetic radiation to ensure the constancy of the surface area of each partial region acted on in each partial exposure, this last mentioned step further comprising:

employing along said optical axis in a direction of pulse propogation, a first, stationary optical element for providing a real or virtual image, a second optical element having a convergent conical surface, following said first optical element, which is displaceable along said optical axis, and a third optical element following said second optical element, which is displaceable along said optical axis and has a diverging optical action and a converging cone surface, and moving said second and third optical elements relative to each other, such that with the setting of optional beam cross-sectional parameters, the respective resulting beam cross-sectional area of the emergent beam is essentially constant.

8. Process according to claim 7, wherein said second optical element comprises a planoconvex lens with diverging or converging cone action.

9. Process according to claim 7, wherein said third optical element comprises a planoconcave lens with converging cone action.

10. Process according to claim 7, wherein said second and third optical elements have mutually facing conical surfaces.

11. Process according to claim 7, further comprising a control device for displacing said second and third optical elements along defined control curves (K2, K3).

12. Process according to claim 7, wherein said second and third optical elements are displaceable along defined control curves (K2, K3) between an initial position determined by $$d_2 = \beta \cdot d_1$$

and $$d_3 = 0$$

and a final position determined by $$d_2 = 0.082 d_1$$

and $$d_3 = 0.122 d_1,$$

wherein $d_1$ is the fixed focal distance of said first stationary optical element, $\beta$ is the telescope factor of said second and third optical elements, $d_2$ is the distance of said second optical element from the focal plane (E1) of said first stationary optical element, and $d_3$ is the distance between said second and said third optical elements.

* * * * *